United States Patent [19]

Inoue et al.

[11] Patent Number: 5,003,083

[45] Date of Patent: Mar. 26, 1991

[54] PROCESS FOR PREPARING OPTICALLY ACTIVE CYANO COMPOUND

[75] Inventors: Kenji Inoue, Kobe; Mitsunori Matsumoto, Takasago; Satomi Takahashi; Takehisa Ohashi, both of Kobe; Kiyoshi Watanabe, Akashi, all of Japan

[73] Assignee: Kanegafuchi Chemical Industry, Co., Ltd., Osaka, Japan

[21] Appl. No.: 131,230

[22] Filed: Dec. 10, 1987

[30] Foreign Application Priority Data

Dec. 15, 1986 [JP] Japan .................. 61-297941

[51] Int. Cl.$^5$ .................. C07D 333/12; C07D 333/20; C07D 307/02; C07C 253/00
[52] U.S. Cl. ..................................... 549/75; 549/495; 558/351
[58] Field of Search .................. 558/351; 549/75, 495

[56] References Cited

U.S. PATENT DOCUMENTS

4,174,459 11/1979 Sakamoto ................. 502/209 X

FOREIGN PATENT DOCUMENTS

| 0109681 | 5/1984 | European Pat. Off. ............ 558/351 |
| 1212954 | 3/1966 | Fed. Rep. of Germany ...... 558/351 |
| 2700167 | 7/1978 | Fed. Rep. of Germany ...... 558/351 |
| 3404858 | 8/1985 | Fed. Rep. of Germany ...... 558/351 |
| 7301736 | 8/1973 | Netherlands ....................... 558/351 |

OTHER PUBLICATIONS

Minamikawa et al., "Asymmetric Hydrocyanation of Aldehydes Using Chiral Titanium Reagents", *Bull. Chem. Soc. Jpn.*, vol. 61, 4379-4383 (1988).

*Tetrahedron Letters*, "Asymmetric Synthesis via Chiral Acetal Templates 7.1 Further Studies on the Cyanation Reaction. The Use of Acetals Derived From Diols With One Chiral Center", vol. 25, No. 6, 1984, pp. 591-594, Pergamon Press Ltd., GB; V. M. F. Choi et al.

*Journal of the Chemical Society*, Chemical Communications, No. 5, 1981, pp. 229,230; J.-I. Oku et al.; "Asymmetric Cyanohydrin Synthesis Catalysed by a Synthetic Cyclic Dipeptide".

*Chemistry Letters*, No. 10, Oct. 1987, pp. 2073-2076, The Chemical Society of Japan; K. Narasaka et al.; "Asymmetric Hydrocyanation of Aldehydes with Cyanotrimethylsilane Promoted by a Chiral Titanium Reagent".

*Journal of the American Chemical Society*, vol. 102, No. 18, 27th Aug. 1980, pp. 5974-5976, American Chem. Society; T. Katsuki et al.; "The First Practical Method for Asymmetric Epoxidation".

*Primary Examiner*—Olik Chaudhuri
*Assistant Examiner*—Andrew Griffis
*Attorney, Agent, or Firm*—Wegner, Cantor, Mueller & Player

[57] ABSTRACT

A novel process for effectively preparing an optically active cyanohydrin comprising asymmetrically cyanating an aldehyde by reacting the aldehyde with a cyanating agent in the presence of a titanate of an optically active tartaric acid derivative.

7 Claims, No Drawings

PROCESS FOR PREPARING OPTICALLY ACTIVE CYANO COMPOUND

BACKGROUND OF THE INVENTION

1. Field of the Invention

The present invention relates to a process for preparing an optically active cyano compound. More particularly, it relates to a process for preparing an optically active cyanohydrin by a novel asymmetric cyanation reaction.

Cyanohydrin is a useful compound in a synthesis of an optically active compound with physiological activity such as a medicine and an agricultural chemical and used as a precursor of α-hydroxy acid or β-aminoalcohol and an intermediate in the synthesis of pyrethroid.

2. Description of the Prior Art

An optically active cyanohydrin has been studied for a long time in view of an asymmetric synthesis, and many synthetic methods such as biochemical methods and a chemical asymmetric syntheses have been developed. However, none of them is industrially successful.

Among the biochemical methods, those utilizing an enzyme in a stereospecific addition of hydrogen cyanide to an aldehyde include (1) a method using emulsin [Fermentforschung, 5, 334 (1922)] and (2) a method using D-oxynitrilase [Angew. Chem., 77, 1139 (1965)], and enzymatic recemic resolution includes (3) a method comprising enzymatic asymmetric hydrolysis of an ester of racemic cyanohydrin with a carboxylic acid which is prepared by a usual chemical synthesis.

Amont the chemical asymmetric synthesis, those comprising asymmetric addition of hydrogen cyanide to an aldehyde in the presence of a basic asymmetric catalyst include (4) a method using a natrual alkaloid such as quinine and quinidine [Biochem. Z., 249, 241 (1932)], (5) a method using optically active polyaziridine [Bull. Chem. Soc. Japan, 38, 354 (1965)], (6) a method using an optically active quaternary ammonium salt phase transfer catalyst [Tetrahedron Letters, 2171 (1979)] and (7) a method using a cyclic peptide including hystidine [J. Chem. Soc., Chem. Comm., 229 (1981)]. Other known methods are (8) a method comprising reacting trimethylsilylcyanide with an optically active acetal of an aldehyde followed by oxidization to cause β-elimination to asymmetrically produce a cyanohydrin [Tetrahedron Letters, 591 (1984)] and (9) a method comprising forming an inclusion compound of brucine and racemic cyanohydrin and accelerating conversion of racemic cyanohydrin to thermodynamically stable one [Chemistry Letters, 661 (1983)].

Although many methods for the synthesis of optically active cyanohydrin have been studied and proposed as described above, all of them have their own drawbacks. For example, the methods (1), (4), (5) and (6) produce a desired product with very low optical purity, the method (2) produces the product with good optical purity but only D-form ((R)-configuration), and the method (3) has difficulty in recovering an unreacted enantiomer. In the methods using the basic asymmetric catalyst, generally the produced cyanohydrin tends to be racemized by the basic catalyst and optical purity of the product decreases as the conversion is increased. Further, the production of the catalysts used in the methods (5) (6) and (7) is difficult.

The method (8) requires troublesome steps and consumes an expensive asymmetric source, and the method (9) can produce only a specific kind of cyanohydrin.

SUMMARY OF THE INVENTION

One object of the present invention is to provide a process for preparing an optically active cyanohydrin, which does not suffer from the drawbacks of the conventional methods.

Accordingly, the present invention provides a process for preparing an optically active cyanohydrin comprising asymmetrically cyanating an aldehyde by reacting the aldehyde with a cyanating agent in the presence of a titanate of an optically active tartaric acid derivative.

DETAILED DESCRIPTION OF THE INVENTION

The reaction of the process according to the present invention may be expressed by the following reaction scheme:

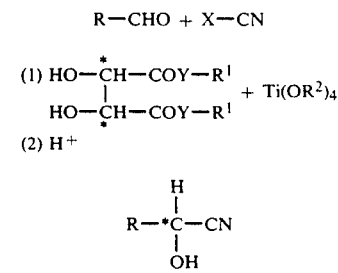

wherein R and $R^1$ are the same or different and substituted or unsubstituted alkyl, aralkyl or aryl, $R^2$ is alkyl, X is hydrogen or trialkylsilyl, Y is oxygen or NZ in which Z is hydrogen, alkyl, aralkyl or aryl or Z and $R^2$ together form a cyclic residue, and * indicates that the asymmetric carbon atom is optically active.

"Alkyl" used herein usually contains 1 to 20 carbon atoms, preferably 1 to 10 carbon atoms. "Aralkyl" used herein usually contains 7 to 26 carbon atoms, preferably 7 to 16 carbon atoms. "Aryl" usually contains 6 to 30 carbon atoms, preferably 6 to 18 carbon atoms.

The optically active titanate formed from a tetraalkyl titanate and the optically active tartaric acid derivative is known as a catalyst which catalyzes asymmetric epoxidation of allyl alcohols with a peroxide, namely so-called Sharpless oxidation (cf. J. Am. Chem. Soc., 102, 5974 (1980)). However, such optically active titanate has not been used in the asymmetric cyanation of aldehyde.

The present invention is based on the finding that the optically active titanate formed from the tetraalkyl titanate and the optically active tartaric acid derivative can effectively catalyze asymmetric cyanation of aldehyde with trialkylsilylcyanide or hydrogen cyanide to give an optically active cyanohydrin with significantly large excess percentage of enantiomer and high yield.

Various combinations of the tetraalkyl titanate and the optically active tartaric acid derivative can be used. Examples of the tetraalkyl titanate are tetramethyl titanate, tetraethyl titanate, tetra-n-propyl titanate, tetra-isopropyl titanate, tetra-n-butyl titanate, tetra-2-ethylhexyl titanate and tetrastearyl titanate. Among them, tetraethyl titanate and tetra-isopropyl titanate are preferred in view of asymmetry of the reaction. As the optically active tartaric acid derviative which acts as an asymmetric ligand, esters and amides of D- or L-tartaric acid are preferred. Examples of the ester are aliphatic or aromatic diesters of tartaric acid such as dimethylester, diethylester, di-n-propylester, di-isopropylester, di-n-butylester, di-isobutylester, di-tert.-butylester, dibenzylester, di-phenylester and di-p-nitrophenylester. Examples of the amide are diamides of tartaric acid with aliphatic or aromatic primary amines such as dimethylamide, diethylamide, di-n-propylamide, di-isopropylamide, di-n-butylamide, di-isobutylamide, di-tert.-butylamide, dibenzylamide, dianilide and diphenethylamide, and diamides of tartaric acid with aliphatic or aromatic secondary amines (e.g. dimethylamine, diethylamine, di-n-propylamine, di-isopropylamine, di-n-butylamine, di-isobutylamine, di-tert.-butylamine, dibenzylamine, pyrrolidine, piperidine and diphenylamine). Among them, diethyl tartarate and di-isopropyl tartarate are preferred in view of asymmetry of the reaction.

Although the optically active titanate may be formed in situ by adding substantially stoichiometric amounts of the tetraalkyl titanate and the optically active tartaric acid derivative to a reaction system, preferably an alcohol emanated from the tetraalkyl titanate is evaporated off together with the solvent from the reaction system under reduced pressure so as to complete the formation of the optically active titanate in view of the yield and the excess percentage of enantiomer in the cyanation reaction.

In the process of the present invention, a wide variety of aldehydes are used insofar as the aldehyde does not have any property which inhibits the reaction. Examples of the aldehyde are alkylaldehydes such as acetaldehyde, propionaldehyde, n-butylaldehyde, isobutylaldehyde, n-valeroaldehyde, isovaleroaldehyde, n-caproaldehyde and n-caprylaldehyde; aralkylaldehydes such as phenylacetoaldehyde, phenylpropionaldehyde and naphthylacetoaldehyde; and arylaldehydes such as benzaldehyde, naphthoaldehyde, furfural and thiophene aldehyde as well as their substitution compounds. Further, unsaturated aldehydes such as acrolein, crotonaldehyde and cinnamaldehyde as well as their substitution compounds may be used.

As a cyanide ion source in the cyanation reaction according to the present invention, any one which supplies the cyanide ion in a non-aqueous system can be used. Examples of the cyanide ion source are hydrogen cyanide and trialkylsilylcyanide.

The cyanation reaction according to the present invention is usually carried out in the presence of an inert solvent. Examples of the solvent are methylene chloride, chloroform, carbon tetrachloride, dichloroethane, trichloroethane, acetonitrile, benzene and toluene. Among them, halogenated hydrocarbons such as methylene chloride and chloroform are preferably used after drying and distillation in view of the yield and the excess percentage of enantiomer.

The reaction temperature for the cyanation reaction according to the present invention is not critical and selected according to other reaction conditions such as the kinds of aldehyde and the tartaric acid derivative. Preferably, the reaction temperature is from −40° C. to +60° C., particularly from −10° C. to +40° C.

The reaction time varies with other reaction conditions such as reaction temperature. In many cases, it is from 30 minutes to 100 hours, preferably from several hours to 20 hours.

To isolate the cyanohydrin from the reaction mixture, a dilute aqueous solution of an acid (e.g. hydrochloric acid, sulfuric acid, nitric acid, etc.) and then vigorously stirred for a period of from 30 minutes to 1 hour at room temperature to hydrolyze the titanate and o-trialkylsilylcyanohydrin which is supposed to be a primary reaction product when trialkylsilylcyanide is used as the cyanide ion source followed by extraction with an organic solvent such as methylene chloride. Then, the product is purified by a conventional method such as the use of a silicagel column or distillation under reduced pressure to obtain the pure cyanohydrin.

PREFERRED EMBODIMENTS OF THE INVENTION

The present invention will be explained further in detail by following Examples.

Example 1

Preparation of R-(+)-α-cyanobenzyl alcohol

To a solution of diisopropyl L(+)-tartarate (515 mg) in absolute dichloromethane (20 ml), tetraisopropyl titanate (568 mg) was dropwise added and stirred for 20 minutes at room temperature. Volatile components were evaporated off from the reaction mixture under reduced pressure at a temperature from room temperature to 35° C. followed by evaporation under reduced pressure for 15 minutes. To the residue, dichloromethane (20 ml) was added and stirred at room temperature to obtain a homogeneous solution. To the resulting solution, trimethylsilylcyanide (218 mg) and then benzaldehyde (212 mg) were added and stirred for 14 hours at 5° C. After the reaction, 1N hydrochloric acid (20 ml) was added and stirred for 30 minutes at room temperature. The mixture was extracted with dichloromethane and dried over sodium sulfate. After evaporating the solvent off to give an oily product, quantitative analysis of the oily product with high performance liquid chromatography (HPLC) (internal standard method) revealed that α-cyanobenzyl alcohol (mandelonitrile) was produced in the yield of 94%, and optical purity analysis with HPLC by using an optical isomer resolution column revealed that it was R(+)-α-cyanobenzyl alcohol with the enantiomer excess percentage of 93%.

The conditions for analyses were as follows:

Quantitative analysis: Column: Finepack SIL $C_{18}$ (Nippon Bunko), (4.6 mmID×250 mm). Mobile phase: Water/acetonitrile (70/30 by volume). Flow rate: 1.5 ml/min. Internal standard: Methyl benzoate. Detection: 210 nm.

Optical purity analysis: Column: CHIRAL CEL-OE (Daicel Chemical Industry) (4.6 mmID×250 mm). Mobile phase: hexane/isopropanol (100/1 by volume). Flow rate: 0.6 ml/min. Detection: 210 nm.

Example 2

Preparation of (R)-(+)-α-cyanobenzyl alcohol

To a solution of L(+)-tartaric acid derivative shown in Table 1 (2 mmol) in a solvent shown in Table 1 (20 ml), a tetraalkyl titanate shown in Table 1 (2 mmol) was dropwise added and stirred for 30 minutes at room temperature. After evaporating volatile components off in the same manner as in Example 1, a solvent shown in Table 1 (20 ml) was added to the residue and stirred at room temperature to obtain a homogeneous solution. To the resulting solution, trimethylsilylcyanide (218 mg) and then benzaldehyde (212 mg) were added and stirred for 14 hours at room temperature. After the reaction, the reaction mixture was treated in the same manner as in Example 1. The product was analyzed by HPLC. The results are shown in Table 1.

in the enantiomer excess percentage of 85% was produced in the yield of 86%.

TABLE 1

| Run No. | Tartaric acid derivative | Titanate | Solvent | Yield of mandelonitrile (%) | Enantiomer excess percentage (%) | Major isomer |
| --- | --- | --- | --- | --- | --- | --- |
| 1 | Diisopropyl tartarate | Ti(Oipr)4 | Dichloromethane | 80 | 88 | R(+) |
| 2 | Diethyl tartarate | Ti(Oipr)4 | Dichloromethane | 87 | 82 | R(+) |
| 3 | Dimethyl tartarate | Ti(Oipr)4 | Dichloromethane | 96 | 16 | R(+) |
| 4 | Dibutyl tartarate | Ti(Oipr)4 | Dichloromethane | 94 | 61 | R(+) |
| 5 | Tartaric dibenzylamide | Ti(Oipr)4 | Dichloromethane | 91 | 57 | (R+) |
| 6 | Tartaric diphenethylamide | Ti(Oipr)4 | Dichloromethane | 95 | 40 | R(+) |
| 7 | Tartaric dipyrrolidineamdie | Ti(Oipr)4 | Dichloromethane | 96 | 7 | S(−) |
| 8 | Diisopropyl tartarate | Ti(Oipr)4 | Chloroform | 88 | 93 | R(+) |
| 9 | Diisopropyl tartarate | Ti(OEt)4 | Dichloromethane | 92 | 88 | R(+) |
| 10 | Diethyl tartarate | Ti(Oipr)4 | Chloroform | 80 | 87 | R(+) |
| 11 | (None) | Ti(Oipr)4 | Dichloromethane | 90 | 0 | — |
| 12 | (None) | (None) | Dichloromethane | 0 | — | — |

Note:
ipr = isopropyl
Et = ethyl

Example 3

Preparation of (R)-(+)-α-cyanobenzyl alcohol

To a solution of L(+)-diethyl tartarate (412 mg) in absolute dichloromethane (20 ml), tetaraisopropyl titanate (568 mg) was dropwise added and stirred at room temperature for 30 minutes. After evaporating volatile components off in the same manner as in Example 1, to the residue, dichloromethane (20 ml) was added and stirred at room temperature to obtain a homogeneous solution. After cooling the resulting solution to 0° C., hydrogen cyanide (0.4 ml) and then benzaldehyde (212 mg) were added and stirred at room temperature for 15 hours. Thereafter, the reaction mixture was treated in the same manner as in Example 1 and analyzed by HPLC to reveal that α-cyanobenzyl alcohol was produced in the yield of 55% which contained the R(+) isomer with the enantiomer excess percentage of 77%.

Example 4

Preparation of (R)-(+)-α-cyanobenzyl alcohol

To a solution of L(+)-diisopropyl tartarate (235 mg) in absolute dichloromethane (10 ml), tetaraisopropyl titanate (284 mg) was dropwise added and stirred at room temperature for 30 minutes. After evaporating volatile components off in the same manner as in Example 1, dichloromethane (10 ml) was added to the residue and stirred at room temperature to obtain a homogeneous solution. To the resulting solution, trimethylsilylcyanide (436 mg) and then benzaldehyde (424 mg) were added and stirred at room temperature for 15 hours. Thereafter, the reaction mixture was treated in the same manner as in Example 1 and analyzed by HPLC to reveal that α-cyanobenzyl alcohol containing the R(+) isomer in the enantiomer excess percentage of 88% was produced in the yield of 37% based on the amount of the used benzaldehyde and 148% based on the amount of the used catalyst.

Example 5

Preparation of (S)-(−)-α-cyanobenzyl alcohol

In the same manner as in Example 1 but using D-(−)-diethyl tartarate (412 mg) in place of L-(+)-diethyl tartarate, the cyanation of the aldehyde and post-treatment were carried out. The HPLC analyses revealed that α-cynobenzyl alcohol containing the S(−) isomer Example 6

Preparation of (R)-(+)-α-cyano-3-phenoxybenzyl alcohol

To a solution of L-(+)-diisopropyl tartarate (1.030 mg, 4.4 mmol) in absolute chloroform (40 ml), tetaraisopropyl titanate (1.136 mg, 4 mmol) was dropwise added and stirred at room temperature for 30 minutes. After evaporating volatile components off in the same manner as in Example 1, absolute chloroform (40 ml) was added to the residue and stirred at room temperature to obtain a homogeneous solution. To the resulting solution, trimethylsilyl cyanide (436 mg, 4.4 mmol) and then 3-phenoxybenzaldehyde (793 mg, 4 mmol) were added and stirred at room temperature for 14 hours. Thereafter, 1N hydrochloric acid (40 ml) was added and stirred at room temperature for 30 minutes. Then, the reaction mixture was extracted with dichloromethane and dried over sodium sulfate followed by evaporation of the solvent to give an oily product. The product was purified by column chromatography (silica gel, eluent: hexane/ethyl acetate) to obtain α-cyano-3-phenoxybenzyl alcohol (580 mg).

The optical rotatory power of this product ($[\alpha]_D^{20} = 13.82°$ (benzene, c=1.11)) indicated that (R)-(+)-α-cyano-3-phenoxybenzyl alcohol was predominantly produced in the enantiomer excess percentage of 84%.

Example 7

Preparation of (S)-(−)-1-cyano-3-phenylpropyl alcohol

In the same manner as in Example 6 but using 3-phenylpropionaldehyde (537 mg, 4 mmol) in place of 3-phenoxybenzaldehyde, the cyanation and post treatment were carried out. The crude product was purified by column chromatography (silica gel, eluent: hexane/ethyl acetate) to obtain α-cyano-3-phenylpropyl alcohol (519 mg). Yield, 80%. $[\alpha]_D^{20} = -5.08°$ (benzene, c=0.944).

α-Cyano-3-phenylpropyl alcohol wad hydrolyzed in concentrated hydrochloric acid (0.5 ml) at room temperature for 3 days with stirring to convert it to 1-hydroxy-4-phenyl butyric acid which was isolated by crystallization from benzene. $[\alpha]_D^{20} = 7.02°$ (ethanol, c=0.968).

The optical purity of the isolated crystalline product was 68% e.e based on the optical rotatory power of (S)-1-hydroxy-4-phenyl butyric acid ($[\alpha]_D^{20} = 10.4°$ (ethanol)) (cf. F. Nerdel and H. Rachel, Chem. Ber., 89, 671 (1956)).

Example 8

Preparation of D-(+)-1-cyano-3-methylbutyl alcohol

In the same manner as in Example 6 but using isoveleraldehyde (345 mg) in place of 3-phenoxybenzaldehyde, the cyanation and post-treatment were carried out. The crude product was purified by Kugel distillation at 110°-120° C./3 mm to obtain 1-cyano-3-methylbutyl alcohol as an oily product (294 mg). Yield, 65%. $[\alpha]_D^{20} = 23.5°$ (benzene, c=1.03).

α-Cyano-3-methylbutyl alcohol wad hydrolyzed in concentrated hydrochloric acid (0.5 ml) at room temperature for 5 days with stirring to convert it to 2-hydroxyisocaproic acid, which was isolated in a crystalline form. $[\alpha]_D^{22} = 21.4°$ (1N NaOH, c=1.14).

The optical purity of the crystalline product was 77% e.e. based on the optical rotatory power of L-(−)-2-hydroxyisocaproic acid ($[\alpha]_D^{20} = -27.7°$ 1N NaOH, c=1)) (cf. H. Scheibler and A. S. Wheeler, Ber., 44, 2684 (1911)).

Example 9

In the same manner as in Example 6 but using trans-cinnamaldehyde (528 mg) in place of 3-phenoxybenzaldehyde, the cyanation and post-treatment were carried out. The crude product was purified by column chromatography (silica gel, eluent: hexane/ethyl acetate) to obtain crystalline optically active trans-α-cyanocinnamic alcohol (382 mg). Yield, 62%. $[\alpha]_D^{20} = 7.92°$ (ethanol, c=1.06).

$^1$H-NMR (CDCl$_3$): δ (ppm)=3.23 (br, s, 1H), 5.01–5.30 (m, 1H), 6.22 (dd, 1H, J=15 Hz and 6 Hz), 6.90 (d, 1H, J=15 Hz), 7.23–7.67 (m, 5H).

Example 10

Preparation of (+)-α-cyano-2-thiophene methanol

In the same manner as in Example 6 but using 2-thiophenealdehyde (449 mg) in place of 3-phenoxybenzaldehyde, the cyanation and post-treatment were carried out. The crude product was purified by column chromatography (silica gel, eluent: hexane/ethyl acetate) to obtain optically active α-cyano-2-thiophene methanol (363 mg). Yield, 68%. $[\alpha]_D^{20} = 35.6°$ (ethanol, c=1.079). 89% e.e. (according to optical active column analysis)

$^1$H-NMR (CDCl$_3$): δ (ppm)=3.57–4.00 (m, 1H), 5.71 (s, 1H), 6.93–7.14 (m, 1H), 7.17–7.50 (m, 2H).

What is claimed is:

1. A process for preparing an optically active cyanohydrin comprising asymmetrically cyanating an aldehyde by reacting the aldehyde with a cyanating agent in the presence of a titanate of an optically active tartaric acid derivative.

2. The process according to claim 1, wherein the titanate is an optically active titanate prepared from an ester or amide of an optically active tartaric acid and tetraalkyl titanate.

3. The process according to claim 2, wherein the optically active titanate is prepared from optically active diisopropyl titanate and tetraisopropyl titanate.

4. The process according to claim 1, wherein the cyanating agent is trialkylsilylcyanide.

5. The process according to claim 4, wherein the trialkylsilylcyanide is trimethylsilylcyanide.

6. The process according to claim 1, wherein the cyanating agent is hydrogen cyanide.

7. The process according to claim 1, wherein the cyanation is carried out in the presence of halogenated hydrocarbon as a solvent.

* * * * *